US00PP11067P

United States Patent [19]

Fear et al.

[11] Patent Number: Plant 11,067

[45] Date of Patent: Sep. 28, 1999

[54] RASPBERRY PLANT NAMED 'GLORIA'

[75] Inventors: Carlos D. Fear, Aptos, Calif.; Mella-Dee M. Mayberry, Georgetown, Del.

[73] Assignee: Sweetbriar Development, Inc., Watsonville, Calif.

[21] Appl. No.: 09/019,176

[22] Filed: Feb. 5, 1998

[51] Int. Cl.[6] ..... A01H 5/00

[52] U.S. Cl. ..... Plt./204

[58] Field of Search ..... Plt./204

[56] References Cited

U.S. PATENT DOCUMENTS

P.P. 9,340 10/1995 Wilhelm et al. ..... Plt./204

*Primary Examiner*—Howard J. Locker
*Assistant Examiner*—Wendy A Baker
*Attorney, Agent, or Firm*—Pennie & Edmonds LLP

[57] ABSTRACT

The present invention relates to a new and distinct cultivar of red raspberry plant named 'Gloria', botanically identified as *Rubus idaeus* L. The new cultivar is distinguished from other red fruited cultivars by its fruit of bright color, excellent fruit firmness, its very early primocane crop, and high primocane and floricane crop yield.

2 Drawing Sheets

BACKGROUND OF THE INVENTION

The new cultivar 'Gloria', was developed from the hybridization of the selection 'H374-2' (an unpatented variety) as the seed plant with the selection 'Summit' (an unpatented variety) as the pollen plant. The parents were crossed in the Fall of 1992, whereafter fruit and seed were collected to produce seedlings for field planting in Watsonville, Calif. in 1992. The new cultivar was selected from these seedlings in July 1993 for its early primocane crop and firm, attractive fruit. The new cultivar was grown and asexually propagated by in vitro shoot tip culture, root sucker division, and root cuttings at the Cassin Ranch in Santa Cruz County, Calif., and has been shown to maintain the desired and distinguishing characteristics after propagation over several generations.

SUMMARY OF THE INVENTION

The present invention provides a new and distinct red raspberry plant named 'Gloria'. The cultivar is botanically identified as *Rubus idaeus* L. The 'Gloria' cultivar produces a primocane crop which begins in late June and continues until late October. The floricane crop begins in mid May and continues to mid July. This cultivar is distinguished by its very firm, bright fruit and its short cycle from planting to harvest of the primocane crop, its early primocane crop, and high primocane and floricane copy yield.

BRIEF DESCRIPTION OF THE DRAWINGS

The accompanying photographs show typical specimens of the primocane fruit, leaves and shoot of the new variety, in color as nearly true as it is reasonably possible to make in color illustrations of these characteristics.

DETAILED BOTANICAL DESCRIPTION OF THE INVENTION

Figure 1:
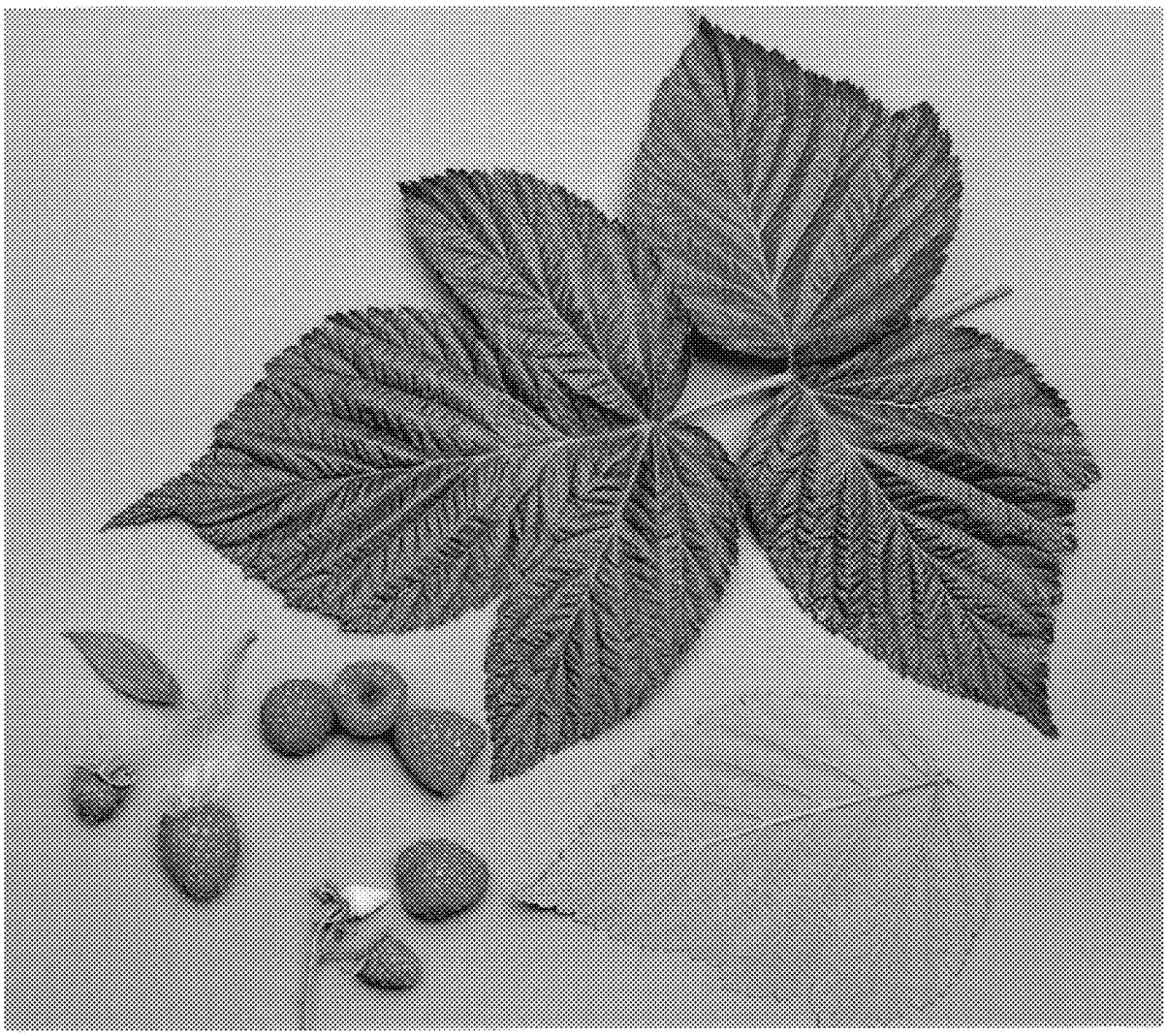
FIG. 1 is a photograph of a primocane mature leaf and fruit.
Figure 2:
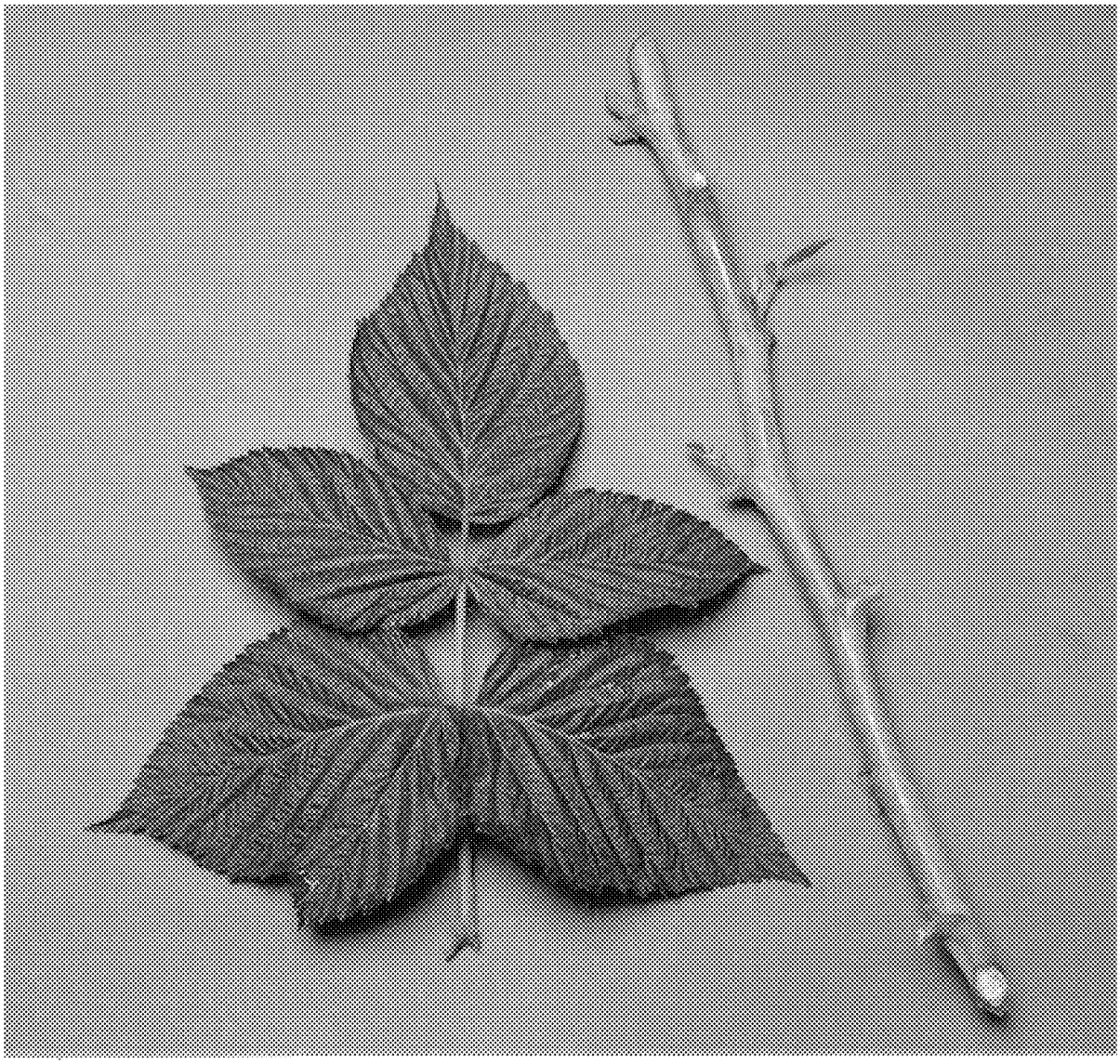
FIG. 2 is a photograph of primocane shoot and leaf.

The following detailed description of the new raspberry cultivar, 'Gloria', is based upon observations taken of plants and fruit grown in Watsonville, Calif. between 1994 and 1997, and is believed to aply to plants of the 'Gloria' cultivar grown in similar conditions of soil and climate elsewhere.

Throughtout this specification, color names beginning with a small letter signifying that the name of the color, as used in common speech, is aptly descriptive. Color names beginning with a capital letter and followed by an alphanumeric code designating the color according to the R.H.S. Colour Chart published by The Royal Horticultural Society of London, England. Color designations, color descriptions, and other phenotypical descriptions may deviate from the stated values and descriptions depending upon variation in environmental, seasonal, climatic and cultural conditions.

Tables 1 and 2 provide information on the plant and fruit characteristics of the new cultivar 'Gloria' compared with characteristics of the unpatented raspberry cultivars 'Hertiage', 'Summit' and 'Amity'. The cultivar closest to 'Gloria' is 'Summit' in fruit characteristics and production cycles. Observations of the cultivars were made under similar conditions.

The new variety is distinguished from other red raspberry cultivars by its fruit of bright color, excellent fruit firmness and its very early primocane crop.

The fruit color of 'Gloria' is a medium bright red with little post harvest color change. Fruit of 'Gloria' is very firm at harvest.

'Gloria' is characterized by a short cycle of days from planting to harvest. The primocane harvest begins in late June which is earlier compared to other varieties that begin primocane harvest in mid to late July. 'Gloria' is also characterized by high primocane and floricane crop yields compared to 'Amity' and 'Heritage'.

'Gloria' is distinguished from its pollen parent, 'Summit', by having an earlier and longer primocane fruiting period, better flavor, and higher yields. The new cultivar is distinguished from its seed parent, 'H374-2', by having firmer fruit and an earlier primocane fruiting cycle.

ISOZYME CHARACTERISTICS

In addition to the morphological description above, the new 'Gloria' cultivar has been analyzed to obtain an indication of its genetic makeup to provide further means for identifying the new variety and distinguishing it from some other somewhat similar and/or related raspberry varieties. Specifically, leaf samples of 'Gloria' and the unpatented varieties of 'Summit' and 'Heritage' were analyzed by electrophoresis according to the procedures of J.C. Cousineau and D.J. Donnelly, "Use of isozyme analysis to characterize raspberry cultivars and detect cultivar mislabeling", *Hort Science* 27:1023–1025 (992). The results of the electrophoretic analysis for the cultivars are presented in Table 3, with the letters representing the banding patterns as described in the above-identified article.

DISEASE AND STRESS RESISTANCE

The cultivar is moderately susceptible to late leaf rust. Resistance is unknown to powdery mildew and root rots. Cold tolerance of the new cultivar has not been established. Post harvest fruit rot resistance is average in comparisons over many selections and varieties.

TABLE 1

PLANT CHARACTERISITCS OF 'GLORIA'

| | Gloria | Heritage | Summit | Amity |
|---|---|---|---|---|
| General | | | | |
| Plant size | medium | large | small–medium | medium |
| Growth habit | erect | erect | semi-erect | erect |
| Productivity | high | medium | high | low–medium |
| Self-fruitfulness | self-fruitful | self-fruitful | self-fruitful | self-fruitful |
| Primocane fruiting | | | | |
| percent of cane flowering as primocane | ~50–70 | ~5–20 | ~40–50 | ~20–35 |
| percent of total yield | ~50–60 | ~40–60 | ~50–70 | ~40–50 |
| Number of young shoots | many | medium | few | many |
| Primocanes | | | | |
| number fruiting laterals/cane | 10–15 (mean 13) | 2–14 (mean 8) | 9–15 (mean 12) | 6–14 (mean 10) |
| number of canes/crown | 2–4 (mean 3) | 3–5 (mean 4) | 2–7 (mean 3) | 1–6 (mean 3) |
| young shoot pigmentation | weak intensity red | medium intensity red | medium intensity red | medium intensity red |
| length (cm) | 173–222 (mean 197) | 182–230 (mean 208) | 137–212 (mean 164) | 135–208 (mean 168) |
| diameter (end of 1st year) | | | | |
| cane base (cm) | 0.8–1.3 (mean 1.1) | 0.9–1.4 (mean 1.2) | 0.8–1.3 (mean 1.1) | 0.8–1.5 (mean 1.1) |
| central ⅓ of cane (cm) | 0.7–1.1 (mean 0.9) | 0.8–1.1 (mean 1.0) | 0.7–1.0 (mean 0.8) | 0.6–1.0 (mean 0.8) |
| time of shoot emergence | medium | very late | late | medium |
| prickles | | | | |
| pigmentation | green–brownish green | green–brownish green | brownish purple–purple | purple |
| density on young shoots | dense | dense | sparse | sparse |
| attitude of tip | downward | downward | downward | horizontal |
| size | medium | medium | medium | small |
| texture | soft | rigid | heavy | heavy |
| presence and distribution on petioles | regularly distributed | regularly distributed | regularly distributed | regularly distributed |
| pubescence on canes | strong | absent or very weak | medium | medium |
| internodal distance (cm) | | | | |
| (at central ⅓ of cane) | 3.0–6.0 (mean 4.5) | 3.0–6.0 (mean 4.7) | 3.2–7.5 (mean 4.8) | 3.0–6.5 (mean 5.0) |
| lenticels | not visible | not visible | not visible | not visible |
| Floricanes | | | | |
| number nodes/lateral branch | 11–17 | 10–14 | 10–15 | 12–19 |
| number of flowers/node | 1–2 | 1–4 | 2–6 | 1–2 |
| Leaves | | | | |
| Arrangement | compound | compound | compound | compound |
| Relief between veins | strong | very weak | medium | medium |
| Cross section | flat | concave | flat | concave–flat |
| Leaflet number | 3–5 | 3–5 | usually 5 | usually 3 |
| Terminal leaflet | | | | |
| length (cm) | 12.8 | 14.6 | 12.4 | 13.7 |
| width (cm) | 7.8 | 7.8 | 7.2 | 12.1 |
| shape | ovate | ovate | ovate | lobed |
| tip | acuminate | acuminate | acuminate | acuminate |
| base | round–cordate | acute | rounded | cordate |
| margin | doubly serrate | doubly serrate | doubly serrate | doubly serrate |
| Lateral leaflets (basal pair) | | | | |
| overlap | overlapping | free | overlapping | overlapping |
| orientation | opposite | opposite | opposite | opposite |
| shape | oblique | oblique | ovate–lobed | ovate–lobed |
| tip | acuminate | acuminate | acuminate | acuminate |
| base | oblique | oblique | oblique–rounded | oblique |
| margin | doubly serrate | doubly serrate | doubly serrate | doubly serrate |
| length (cm) | 11.4 | 14.7 | 11.6 | 11.7 |
| width (cm) | 7.8 | 8.6 | 7.7 | 8.2 |
| Rachis length between terminal leaflet and adjacent lateral leaflets (cm) | 0.8–2.3 (mean 1.4) | 0.8–2.2 (mean 1.5) | 0.5–1.8 (mean 1.2) | 2.4–3.9 (mean 3.0) |
| Glossiness | medium | medium | medium | dull |
| Color | | | | |
| face | medium 147A | medium 137A, 139A | medium 137A | medium 147A |
| underside | 138B | 148C, 191B | 191B | 191A |
| Petiole | | | | |
| length (cm) | 4.9–7.8 (mean 6.3) | 6.6–8.5 (mean 7.6) | 5.8–8.9 (mean 7.4) | 4.0–8.2 (mean 6.0) |
| pigmentation of upper surface | unpigmented | lightly | lightly | lightly |
| pigmentation underside | unpigmented | unpigmented | lightly | unpigmented |
| Petiolule length | very short | very short | short | very short |
| Stipule orientation | erect–relfexed | erect | erect–clasping | erect–clasping |
| Flowers | | | | |
| Flower color | white | white | white | white |

TABLE 1-continued

PLANT CHARACTERISITCS OF 'GLORIA'

| | Gloria | Heritage | Summit | Amity |
|---|---|---|---|---|
| Flowering period | | | | |
| primocane | early June–mid September | mid June–early October | early June–mid September | early June–early October |
| floricane | early April–mid June | early April–early June | early April–early June | early to mid March–early June |
| Flower size | large | small | medium | large |
| Petal | | | | |
| length (cm) | 0.8–1.0 | 0.7–0.8 | 0.7–0.9 | 0.7–1.0 |
| width (cm) | 0.3–0.4 | 0.3 | 0.3–0.4 | 0.3–0.5 |
| Pedicel | | | | |
| coloration | present, medium intensity red | present, strong intensity red | present, strong intensity red | present, medium intensity red |
| length | medium | medium | medium | long |
| Productivity | | | | |
| Primocane | ~8.8 t/acre | ~5.1 t/acre | ~7.3 t/acre | ~6.4 t/acre |
| Floricane | ~6.8 t/acre | ~4.1 t/acre | ~2.9 t/acre | ~5.1 t/acre |

TABLE 2

FRUIT CHARACTERISITCS OF 'GLORIA'

| Fruit | Gloria | Heritage | Summit | Amity |
|---|---|---|---|---|
| Harvest season | | | | |
| primocane | late June–late October | late July–mid November | mid July–late October | mid July–mid November |
| floricane | mid May–mid July | mid May–mid July | mid May–mid July | late April–mid July |
| Color | Medium Red | Medium Red | Medium Red | Medium Red |

TABLE 2-continued

FRUIT CHARACTERISITCS OF 'GLORIA'

| Fruit | Gloria | Heritage | Summit | Amity |
|---|---|---|---|---|
| immature | 41B | 53A | 46A | 46A |
| maturing | 47A, 47B | 45A, 46D | 45A | 47A |
| mature | 46A | 44C | 42B | 42B |
| Glossiness | strong | medium | medium | medium |
| Dimensions | | | | |
| weight (g/fruit) | | | | |
| primocane | 3.0–3.7 (mean 3.3) | 2.7–2.9 (mean 2.8) | 2.5–3.3 (mean 2.8) | 2.7–3.7 (mean 3.2) |
| floricane | 2.7–3.2 (mean 3.0) | 2.3–2.7 (mean 2.6) | 2.5–2.8 (mean 2.6) | 3.0–3.4 (mean 3.2) |
| length (primocane) (mm) | 17.5–24.6 (mean 21.1) | — | 17.5–25.4 (mean 20.2) | 17.5–22.2 (mean 20.1) |
| width (primocane) (mm) | 18.3–23.8 (mean 21.0) | — | 18.3–23.0 (mean 20.4) | 15.9–23.0 (mean 20.2) |
| Soluble solids (%) | 9.5 | — | 9.4 | 9.7 |
| Titratable acidity (% as citric acid) | 12.7 | — | 14.5 | 11.2 |
| Seeds | | | | |
| weight (mg) | 1.5 | — | 1.8 | 1.5 |
| Number druplets/fruit | 49–127 (mean 102) | 45–102 (mean 72) | 73–119 (mean 98) | 62–108 (mean 88) |
| Firmness | firm | firm | firm | firm |
| Yield | high | medium | high | medium |

TABLE 3

ISOZYME BANDING PATTERNS OF 'GLORIA' COMPARED WITH 'HERITAGE' AND 'SUMMIT'

| | Isozyme and Pattern | | |
|---|---|---|---|
| Cultivar | PGI | MDH | PGM |
| Gloria | D | C | A |
| Heritage | A | D | C |
| Summit | A | C | A |

We claim:

1. A new and distinctive cultivar of raspberry plant, as illustrated and described herein.

* * * * *